US009318094B2

(12) United States Patent
Hendrix et al.

(10) Patent No.: US 9,318,094 B2
(45) **Date of Patent: *Apr. 19, 2016**

(54) ADAPTIVE NOISE CANCELING ARCHITECTURE FOR A PERSONAL AUDIO DEVICE

(75) Inventors: Jon D. Hendrix, Wimberly, TX (US); Gautham Devendra Kamath, Austin, TX (US); Nitin Kwatra, Austin, TX (US); Ali Abdollahzadeh Milani, Austin, TX (US); Jeffrey Alderson, Austin, TX (US)

(73) Assignee: CIRRUS LOGIC, INC., Austin, TX (US)

( * ) Notice: Subject to any disclaimer, the term of this patent is extended or adjusted under 35 U.S.C. 154(b) by 443 days.

This patent is subject to a terminal disclaimer.

(21) Appl. No.: 13/413,920

(22) Filed: Mar. 7, 2012

(65) Prior Publication Data

US 2012/0308025 A1 Dec. 6, 2012

Related U.S. Application Data

(60) Provisional application No. 61/493,162, filed on Jun. 3, 2011.

(51) Int. Cl.

*A61F 11/06* (2006.01)
*G10K 11/178* (2006.01)

(Continued)

(52) U.S. Cl.

CPC ...... *G10K 11/1784* (2013.01); *G10K 2210/108* (2013.01); *G10K 2210/3026* (2013.01);

(Continued)

(58) Field of Classification Search

CPC ............ G10K 11/178; G10K 11/1784; G10K 2210/108; G10K 2210/30232; G10K 2210/3026–2210/3028; G10K 2210/3051; G10K 2210/3055; G10K 2210/503; G10K 2210/10; H04R 1/1083; H04R 3/005

USPC ............... 381/71.1–71.14, 94.1, 57, 74, 73.1, 381/122; 704/226; 700/94; 455/570, 569.1; 341/123, 122

See application file for complete search history.

(56) References Cited

U.S. PATENT DOCUMENTS 4,020,567 A 5/1977 Webster
4,926,464 A 5/1990 Schley-May (Continued)

FOREIGN PATENT DOCUMENTS

DE 102011013343 A1 9/2012
EP 0412902 A2 2/1991

(Continued)

OTHER PUBLICATIONS

U.S. Appl. No. 14/029,159, filed Sep. 17, 2013, Li, et al.

(Continued)

*Primary Examiner* — Vivian Chin
*Assistant Examiner* — Con P Tran
(74) *Attorney, Agent, or Firm* — Mitch Harris, Atty at Law, LLC; Andrew M. Harris

(57) ABSTRACT

A personal audio device, such as a wireless telephone, includes an adaptive noise canceling (ANC) circuit that adaptively generates an anti-noise signal from a reference microphone signal that measures the ambient audio and an error microphone signal that measures the output of an output transducer plus any ambient audio at that location and injects the anti-noise signal at the transducer output to cause cancellation of ambient audio sounds. A processing circuit uses the reference and error microphone to generate the anti-noise signal, which can be generated by an adaptive filter operating at a multiple of the ANC coefficient update rate. Downlink audio can be combined with the high data rate anti-noise signal by interpolation. High-pass filters in the control paths reduce DC offset in the ANC circuits, and ANC coefficient adaptation can be halted when downlink audio is not detected.

27 Claims, 5 Drawing Sheets

(51) Int. Cl.
*H04R 3/00* (2006.01)
*H04R 1/10* (2006.01)

(52) U.S. Cl.
CPC *G10K2210/3051* (2013.01); *G10K 2210/3055* (2013.01); *H04R 1/1083* (2013.01); *H04R 3/005* (2013.01)

(56) References Cited

U.S. PATENT DOCUMENTS 4,998,241 A 3/1991 Brox et al.
5,018,202 A 5/1991 Takahashi
5,021,753 A 6/1991 Chapman
5,044,373 A 9/1991 Northeved et al.
5,117,401 A 5/1992 Feintuch
5,251,263 A 10/1993 Andrea et al.
5,278,913 A 1/1994 Delfosse et al.
5,321,759 A 6/1994 Yuan
5,337,365 A 8/1994 Hamabe et al.
5,359,662 A 10/1994 Yuan et al.
5,377,276 A 12/1994 Terai et al.
5,386,477 A 1/1995 Popovich et al.
5,410,605 A 4/1995 Sawada et al.
5,425,105 A 6/1995 Lo et al.
5,445,517 A 8/1995 Kondou et al.
5,465,413 A 11/1995 Enge et al.
5,481,615 A 1/1996 Eatwell et al.
5,548,681 A 8/1996 Gleaves et al.
5,550,925 A 8/1996 Hori et al.
5,559,893 A 9/1996 Krokstad et al.
5,586,190 A 12/1996 Trantow et al.
5,640,450 A 6/1997 Watanabe
5,668,747 A 9/1997 Ohashi
5,687,075 A 11/1997 Stothers
5,696,831 A 12/1997 Inanaga et al.
5,699,437 A 12/1997 Finn
5,706,344 A 1/1998 Finn
5,740,256 A 4/1998 Castello Da Costa et al.
5,768,124 A 6/1998 Stothers et al.
5,815,582 A 9/1998 Claybaugh et al.
5,832,095 A 11/1998 Daniels
5,852,667 A 12/1998 Pan et al.
5,909,498 A 6/1999 Smith
5,940,519 A 8/1999 Kuo
5,946,391 A 8/1999 Dragwidge et al.
5,991,418 A 11/1999 Kuo
6,041,126 A 3/2000 Terai et al.
6,118,878 A 9/2000 Jones
6,181,801 B1 1/2001 Puthuff et al.
6,219,427 B1 4/2001 Kates et al.
6,278,786 B1 8/2001 McIntosh
6,282,176 B1 8/2001 Hemkumar
6,304,179 B1 10/2001 Lolito et al.
6,317,501 B1 11/2001 Matsuo
6,418,228 B1 7/2002 Terai et al.
6,434,246 B1 8/2002 Kates et al.
6,434,247 B1 8/2002 Kates et al.
6,445,799 B1 9/2002 Taenzer et al.
6,522,746 B1 2/2003 Marchok et al.
6,542,436 B1 4/2003 Myllyla
6,650,701 B1 11/2003 Hsiang et al.
6,683,960 B1 1/2004 Fujii et al.
6,738,482 B1 5/2004 Jaber
6,766,292 B1 7/2004 Chandran
6,768,795 B2 7/2004 Feltstrom et al.
6,792,107 B2 9/2004 Tucker et al.
6,850,617 B1 2/2005 Weigand
6,940,982 B1 9/2005 Watkins
7,016,504 B1 3/2006 Shennib
7,058,463 B1 * 6/2006 Ruha et al. ...................... 700/94
7,103,188 B1 9/2006 Jones
7,181,030 B2 2/2007 Rasmussen et al.
7,330,739 B2 2/2008 Somayajula
7,365,669 B1 4/2008 Melanson
7,466,838 B1 12/2008 Mosely
7,680,456 B2 3/2010 Muhammad et al.
7,742,746 B2 6/2010 Xiang et al.
7,742,790 B2 6/2010 Konchitsky et al.
7,817,808 B2 10/2010 Konchitsky et al.
7,953,231 B2 5/2011 Ishida
8,019,050 B2 9/2011 Mactavish et al.
8,085,966 B2 12/2011 Amsel
D666,169 S 8/2012 Tucker et al.
8,249,262 B2 8/2012 Chua et al.
8,251,903 B2 8/2012 LeBoeuf et al.
8,290,537 B2 10/2012 Lee et al.
8,325,934 B2 12/2012 Kuo
8,331,604 B2 12/2012 Saito et al.
8,374,358 B2 2/2013 Buck et al.
8,379,884 B2 2/2013 Horibe et al.
8,401,200 B2 3/2013 Tiscareno et al.
8,442,251 B2 5/2013 Jensen et al.
8,559,661 B2 10/2013 Tanghe
8,600,085 B2 12/2013 Chen et al.
8,775,172 B2 7/2014 Konchitsky et al.
8,804,974 B1 8/2014 Melanson
8,831,239 B2 9/2014 Bakalos
8,842,848 B2 9/2014 Donaldson et al.
8,855,330 B2 10/2014 Taenzer
8,908,877 B2 12/2014 Abdollahzadeh Milani et al.
8,942,976 B2 1/2015 Li et al.
8,977,545 B2 3/2015 Zeng et al.
9,066,176 B2 6/2015 Hendrix et al.
9,071,724 B2 6/2015 Do et al.
9,082,391 B2 7/2015 Yermeche et al.
9,129,586 B2 9/2015 Bajic et al.
2001/0053228 A1 12/2001 Jones
2002/0003887 A1 1/2002 Zhang et al.
2003/0063759 A1 4/2003 Brennan et al.
2003/0072439 A1 4/2003 Gupta
2003/0185403 A1 10/2003 Sibbald
2004/0047464 A1 3/2004 Yu et al.
2004/0120535 A1 6/2004 Woods
2004/0165736 A1 8/2004 Hetherington et al.
2004/0167777 A1 8/2004 Hetherington et al.
2004/0202333 A1 10/2004 Csermak et al.
2004/0240677 A1 12/2004 Onishi et al.
2004/0242160 A1 12/2004 Ichikawa et al.
2004/0264706 A1 12/2004 Ray et al.
2005/0004796 A1 1/2005 Trump et al.
2005/0018862 A1 1/2005 Fisher
2005/0117754 A1 6/2005 Sakawaki
2005/0207585 A1 9/2005 Christoph
2005/0240401 A1 10/2005 Ebenezer
2006/0018460 A1 1/2006 McCree
2006/0035593 A1 2/2006 Leeds
2006/0055910 A1 3/2006 Lee
2006/0069556 A1 3/2006 Nadjar et al.
2006/0153400 A1 7/2006 Fujita et al.
2006/0159282 A1 7/2006 Borsch
2006/0161428 A1 7/2006 Fouret
2006/0251266 A1 11/2006 Saunders et al.
2007/0030989 A1 2/2007 Kates
2007/0033029 A1 2/2007 Sakawaki
2007/0038441 A1 2/2007 Inoue et al.
2007/0047742 A1 3/2007 Taenzer et al.
2007/0053524 A1 3/2007 Haulick et al.
2007/0076896 A1 4/2007 Hosaka et al.
2007/0154031 A1 7/2007 Avendano et al.
2007/0258597 A1 11/2007 Rasmussen et al.
2007/0297620 A1 12/2007 Choy
2008/0019548 A1 1/2008 Avendano
2008/0101589 A1 5/2008 Horowitz et al.
2008/0107281 A1 5/2008 Togami et al.
2008/0144853 A1 6/2008 Sommerfeldt et al.
2008/0177532 A1 7/2008 Greiss et al.
2008/0181422 A1 7/2008 Christoph
2008/0226098 A1 9/2008 Haulick et al.
2008/0240413 A1 10/2008 Mohammad et al.
2008/0240455 A1 10/2008 Inoue et al.
2008/0240457 A1 10/2008 Inoue et al.
2008/0269926 A1 10/2008 Xiang et al.
2009/0012783 A1 1/2009 Klein
2009/0034748 A1 2/2009 Sibbald

(56) References Cited

U.S. PATENT DOCUMENTS

2009/0041260 A1 2/2009 Jorgensen et al.
2009/0046867 A1* 2/2009 Clemow ........................ 381/71.6
2009/0060222 A1 3/2009 Jeong et al.
2009/0080670 A1 3/2009 Solbeck et al.
2009/0086990 A1 4/2009 Christoph
2009/0175461 A1 7/2009 Nakamura et al.
2009/0175466 A1 7/2009 Elko et al.
2009/0196429 A1 8/2009 Ramakrishnan et al.
2009/0220107 A1 9/2009 Every et al.
2009/0238369 A1 9/2009 Ramakrishnan et al.
2009/0245529 A1 10/2009 Asada et al.
2009/0254340 A1 10/2009 Sun et al.
2009/0290718 A1 11/2009 Kahn et al.
2009/0296965 A1 12/2009 Kojima
2009/0304200 A1 12/2009 Kim et al.
2009/0311979 A1 12/2009 Husted et al.
2010/0002891 A1 1/2010 Shiraishi et al.
2010/0014683 A1* 1/2010 Maeda et al. ................ 381/71.4
2010/0014685 A1 1/2010 Wurm
2010/0061564 A1 3/2010 Clemow et al.
2010/0069114 A1 3/2010 Lee et al.
2010/0082339 A1 4/2010 Konchitsky et al.
2010/0098263 A1 4/2010 Pan et al.
2010/0098265 A1 4/2010 Pan et al.
2010/0124335 A1 5/2010 Wessling et al.
2010/0124336 A1* 5/2010 Shridhar et al. ............. 381/71.4
2010/0124337 A1 5/2010 Wertz et al.
2010/0131269 A1 5/2010 Park et al.
2010/0142715 A1 6/2010 Goldstein et al.
2010/0150367 A1 6/2010 Mizuno
2010/0158330 A1 6/2010 Guissin et al.
2010/0166203 A1 7/2010 Peissig et al.
2010/0195838 A1 8/2010 Bright
2010/0195844 A1* 8/2010 Christoph et al. ......... 381/71.11
2010/0207317 A1 8/2010 Iwami et al.
2010/0239126 A1 9/2010 Grafenberg et al.
2010/0246855 A1 9/2010 Chen
2010/0260345 A1 10/2010 Shridhar et al.
2010/0266137 A1 10/2010 Sibbald et al.
2010/0272276 A1 10/2010 Carreras et al.
2010/0272283 A1 10/2010 Carreras et al.
2010/0274564 A1 10/2010 Bakalos et al.
2010/0284546 A1 11/2010 DeBrunner et al.
2010/0291891 A1 11/2010 Ridgers et al.
2010/0296666 A1 11/2010 Lin
2010/0296668 A1 11/2010 Lee et al.
2010/0310086 A1 12/2010 Magrath et al.
2010/0322430 A1 12/2010 Isberg
2011/0007907 A1* 1/2011 Park et al. .................... 381/71.8
2011/0026724 A1 2/2011 Doclo
2011/0099010 A1 4/2011 Zhang
2011/0106533 A1 5/2011 Yu
2011/0116654 A1 5/2011 Chan et al.
2011/0129098 A1 6/2011 Delano et al.
2011/0130176 A1 6/2011 Magrath et al.
2011/0142247 A1 6/2011 Fellers et al.
2011/0144984 A1 6/2011 Konchitsky
2011/0158419 A1 6/2011 Theverapperuma et al.
2011/0206214 A1 8/2011 Christoph et al.
2011/0222698 A1 9/2011 Asao et al.
2011/0249826 A1 10/2011 Van Leest
2011/0288860 A1 11/2011 Schevciw et al.
2011/0293103 A1 12/2011 Park et al.
2011/0299695 A1* 12/2011 Nicholson .................... 381/71.6
2011/0305347 A1 12/2011 Wurm
2011/0317848 A1 12/2011 Ivanov et al.
2012/0135787 A1 5/2012 Kusunoki et al.
2012/0140917 A1 6/2012 Nicholson et al.
2012/0140942 A1 6/2012 Loeda
2012/0140943 A1 6/2012 Hendrix et al.
2012/0148062 A1 6/2012 Scarlett et al.
2012/0155666 A1 6/2012 Nair
2012/0170766 A1* 7/2012 Alves et al. ................ 381/71.11
2012/0215519 A1 8/2012 Park et al.
2012/0250873 A1 10/2012 Bakalos et al.
2012/0259626 A1 10/2012 Li et al.
2012/0263317 A1 10/2012 Shin et al.
2012/0281850 A1 11/2012 Hyatt
2012/0300955 A1 11/2012 Iseki et al.
2012/0300958 A1 11/2012 Klemmensen
2012/0300960 A1 11/2012 Mackay et al.
2012/0308021 A1 12/2012 Kwatra et al.
2012/0308024 A1 12/2012 Alderson et al.
2012/0308026 A1 12/2012 Kamath et al.
2012/0308027 A1 12/2012 Kwatra
2012/0308028 A1* 12/2012 Kwatra et al. ............. 381/71.11
2012/0310640 A1 12/2012 Kwatra et al.
2013/0010982 A1 1/2013 Elko et al.
2013/0083939 A1 4/2013 Fellers et al.
2013/0195282 A1 8/2013 Ohita et al.
2013/0243198 A1 9/2013 Van Rumpt
2013/0243225 A1 9/2013 Yokota
2013/0272539 A1 10/2013 Kim et al.
2013/0287218 A1 10/2013 Alderson et al.
2013/0287219 A1 10/2013 Hendrix et al.
2013/0301842 A1 11/2013 Hendrix et al.
2013/0301846 A1 11/2013 Alderson et al.
2013/0301847 A1 11/2013 Alderson et al.
2013/0301848 A1 11/2013 Zhou et al.
2013/0301849 A1 11/2013 Alderson et al.
2013/0315403 A1 11/2013 Samuelsson
2013/0343556 A1 12/2013 Bright
2013/0343571 A1 12/2013 Rayala et al.
2014/0016803 A1 1/2014 Puskarich
2014/0036127 A1 2/2014 Pong et al.
2014/0044275 A1 2/2014 Goldstein et al.
2014/0050332 A1 2/2014 Nielsen et al.
2014/0072134 A1 3/2014 Po et al.
2014/0086425 A1 3/2014 Jensen et al.
2014/0146976 A1 5/2014 Rundle
2014/0169579 A1 6/2014 Azmi
2014/0177851 A1 6/2014 Kitazawa et al.
2014/0211953 A1 7/2014 Alderson et al.
2014/0270222 A1 9/2014 Hendrix et al.
2014/0270223 A1 9/2014 Li et al.
2014/0270224 A1 9/2014 Zhou et al.
2014/0294182 A1 10/2014 Axelsson et al.
2014/0307887 A1 10/2014 Alderson
2014/0307888 A1 10/2014 Alderson et al.
2014/0307890 A1 10/2014 Zhou et al.
2014/0314244 A1 10/2014 Yong
2014/0314247 A1 10/2014 Zhang
2014/0369517 A1 12/2014 Zhou et al.
2015/0092953 A1 4/2015 Abdollahzadeh Milani et al.
2015/0104032 A1 4/2015 Kwatra et al.
2015/0161981 A1 6/2015 Kwatra
2015/0269926 A1 9/2015 Alderson et al.

FOREIGN PATENT DOCUMENTS

EP 1691577 A2 8/2006
EP 1880699 A2 1/2008
EP 1947642 A1 7/2008
EP 2133866 A1 12/2009
EP 2216774 A1 8/2010
EP 2237573 A1 10/2010
EP 2395500 A1 12/2011
EP 2395501 A1 12/2011
EP 2551845 A1 1/2013
GB 2401744 A 11/2004
GB 2436657 A 10/2007
GB 2455821 A 6/2009
GB 2455824 A 6/2009
GB 2455828 A 6/2009
GB 2484722 A 4/2012
JP H06-186985 A 7/1994
JP 07104769 4/1995
JP 07240989 9/1995
JP 07325588 12/1995
JP H11305783 A 11/1999
JP 2008015046 A 1/2008
WO WO 9113429 9/1991
WO WO 9911045 3/1999
WO WO 03/015074 A1 2/2003

(56) References Cited

FOREIGN PATENT DOCUMENTS

| | | | |
|---|---|---|---|
| WO | WO 03015275 | A1 | 2/2003 |
| WO | WO 2004009007 | A1 | 1/2004 |
| WO | WO 2004017303 | A1 | 2/2004 |
| WO | WO 2006128768 | A1 | 12/2006 |
| WO | WO 2007007916 | A1 | 1/2007 |
| WO | WO 2007011337 | | 1/2007 |
| WO | WO 2007110807 | A2 | 10/2007 |
| WO | WO 2007113487 | A1 | 11/2007 |
| WO | WO 2010117714 | A1 | 10/2010 |
| WO | WO 2010131154 | A1 | 11/2010 |
| WO | WO 2012134874 | A1 | 10/2012 |
| WO | WO 2015038255 | A1 | 3/2015 |

OTHER PUBLICATIONS

U.S. Appl. No. 14/062,951, filed Oct. 25, 2013, Zhou, et al.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and The Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
U.S. Appl. No. 13/686,353, filed Nov. 27, 2012, Hendrix, et al.
U.S. Appl. No. 13/795,160, filed Mar. 12, 2013, Hendrix, et al.
U.S. Appl. No. 13/692,367, filed Dec. 3, 2012, Alderson, et al.
U.S. Appl. No. 13/722,119, filed Dec. 20, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/787,906, filed Mar. 7, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
U.S. Appl. No. 13/794,979, filed Mar. 12, 2013, Alderson, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.
Jin, et al. "A simultaneous equation method-based online secondary path modeling algorithm for active noise control", Journal of Sound and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.

(56) References Cited

OTHER PUBLICATIONS

U.S. Appl. No. 13/968,007, filed Aug. 15, 2013, Hendrix, et al.
U.S. Appl. No. 14/197,814, filed Mar. 5, 2014, Kaller, et al.
U.S. Appl. No. 14/210,537, filed Mar. 14, 2014, Abdollahzadeh Milani, et al.
U.S. Appl. No. 14/210,589, filed Mar. 14, 2014, Abdollahzadeh Milani, et al.
Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages. (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.
Widrow, B., et al., Adaptive Noise Cancelling; Principles and Applications, Proceedings of the IEEE, Dec. 1975, pp. 1692-1716, vol. 63, No. 13, IEEE, New York, NY, US.
Morgan, et al., A Delayless Subband Adaptive Filter Architecture, IEEE Transactions on Signal Processing, IEEE Service Center, Aug. 1995, pp. 1819-1829, vol. 43, No. 8, New York, NY, US.
U.S. Appl. No. 14/656,124, filed Mar. 12, 2015, Hendrix, et al.
Parkins, et al., "Narrowband and broadband active control in an enclosure using the acoustic energy density", J. Acoust. Soc. Am. Jul. 2000, pp. 192-203, vol. 108, issue 1, US.
Feng, et al.., "A broadband self-tuning active noise equaliser", Signal Processing, Oct. 1, 1997, pp. 251-256, vol. 62, No. 2, Elsevier Science Publishers B.V. Amsterdam, NL.
Zhang, et al., "A Robust Online Secondary Path Modeling Method with Auxiliary Noise Power Scheduling Strategy and Norm Constraint Manipulation", IEEE Transactions on Speech and Audio Processing, IEEE Service Center, Jan. 1, 2003, pp. 45-53, vol. 11, No. 1, NY.
Lopez-Gaudana, et al., "A hybrid active noise cancelling with secondary path modeling", 51st Midwest Symposium on Circuits and Systems, MWSCAS 2008, Aug. 10-13, 2008, pp. 277-280, IEEE, Knoxville, TN.
International Search Report and Written Opinion in PCT/US2012/035815, mailed Jul. 25, 2013, 22 pages (pp. 1-22 in pdf).
Written Opinion of the International Preliminary Examining Authority in PCT/US2012/035815, mailed on Feb. 26, 2014, 11 pages (pp. 1-11 in pdf).
International Preliminary Report on Patentability in PCT/US2012/035815, mailed on May 14, 2014, 44 pages (pp. 1-44 in pdf).
Rafaely, Boaz, "Active Noise Reducing Headset—an Overview", The 2001 International Congress and Exhibition on Noice Control Engineering, Aug. 27-30, 2001, 10 pages (pp. 1-10 in pdf), The Netherlands.
Ray, et al., "Hybrid Feedforward-Feedback Active Noise Reduction for Hearing Protection and Communication", The Journal of the Acoustical Society of America, American Institute of Physics for the Acoustical Society of America, Jan. 2006, pp. 2026-2036 vol. 120, No. 4, New York, NY.

* cited by examiner

ADAPTIVE NOISE CANCELING ARCHITECTURE FOR A PERSONAL AUDIO DEVICE

This U.S. Patent Application claims priority under 35 U.S.C. §119(e) to U.S. Provisional Patent Application Ser. No. 61/493,162 filed on Jun. 3, 2011.

BACKGROUND OF THE INVENTION

1. Field of the Invention

The present invention relates generally to personal audio devices such as wireless telephones that include adaptive noise cancellation (ANC), and more specifically, to architectural features of an ANC system integrated in a personal audio device.

2. Background of the Invention

Wireless telephones, such as mobile/cellular telephones, cordless telephones, and other consumer audio devices, such as mp3 players, are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

Since the acoustic environment around personal audio devices such as wireless telephones can change dramatically, depending on the sources of noise that are present and the position of the device itself, it is desirable to adapt the noise canceling to take into account such environmental changes. However, adaptive noise canceling circuits can be complex, consume additional power, and can generate undesirable results under certain circumstances.

Therefore, it would be desirable to provide a personal audio device, including a wireless telephone, that provides noise cancellation that is effective, energy efficient, and/or has less complexity.

SUMMARY OF THE INVENTION

The above stated objectives of providing a personal audio device providing effective noise cancellation with lower power consumption and/or lower complexity, is accomplished in a personal audio device, a method of operation, and an integrated circuit.

The personal audio device includes a housing, with a transducer mounted on the housing for reproducing an audio signal that includes both source audio for playback to a listener and an anti-noise signal for countering the effects of ambient audio sounds in an acoustic output of the transducer, which may include the integrated circuit to provide adaptive noise-canceling (ANC) functionality. The method is a method of operation of the personal audio device and integrated circuit. A reference microphone is mounted on the housing to provide a reference microphone signal indicative of the ambient audio sounds. An error microphone is included for controlling the adaptation of the anti-noise signal to cancel the ambient audio sounds and for correcting for the electro-acoustic path from the output of the processing circuit through the environment of the transducer. The personal audio device further includes an ANC processing circuit within the housing for adaptively generating an anti-noise signal from the reference microphone signal and reference microphone using one or more adaptive filters, such that the anti-noise signal causes substantial cancellation of the ambient audio sounds.

The ANC circuit implements an adaptive filter that generates the anti-noise signal that may be operated at a multiple of the ANC coefficient update rate. Sigma-delta modulators can be included in the higher sample rate signal path(s) to reduce the width of the adaptive filter(s) and other processing blocks. High-pass filters in the control paths may be included to reduce DC offset in the ANC circuits, and ANC adaptation can be halted when downlink audio is absent. When downlink audio is present, it can be combined with the high data rate anti-noise signal by interpolation and ANC adaptation is resumed.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise canceling techniques and circuits that can be implemented in a personal audio device, such as a wireless telephone. The personal audio device includes an adaptive noise canceling (ANC) circuit that measures the ambient acoustic environment and generates a signal that is injected in the speaker (or other transducer) output to cancel ambient acoustic events. A reference microphone is provided to measure the ambient acoustic environment and an error microphone is included for controlling the adaptation of the anti-noise signal to cancel the ambient audio sounds and for correcting for the electro-acoustic path from the output of the processing circuit through the transducer. The coefficient control of the adaptive filter that generates the anti-noise signal may be operated at a baseband rate much lower than a sample rate of the adaptive filter, reducing power consumption and complexity of the ANC processing circuits. High-pass filters can be included in the feedback paths that provide the inputs to the coefficient control, to reduce DC offset in the ANC control loop, and the ANC adaptation may be halted when downlink audio is absent, so that adaptation of the adaptive filter does not proceed under conditions that might lead to instability. When downlink audio, which may be provided at baseband and combined with the higher-data rate audio by interpolation, is detected, adaptation of the adaptive filter coefficients is resumed.

Figure 1:
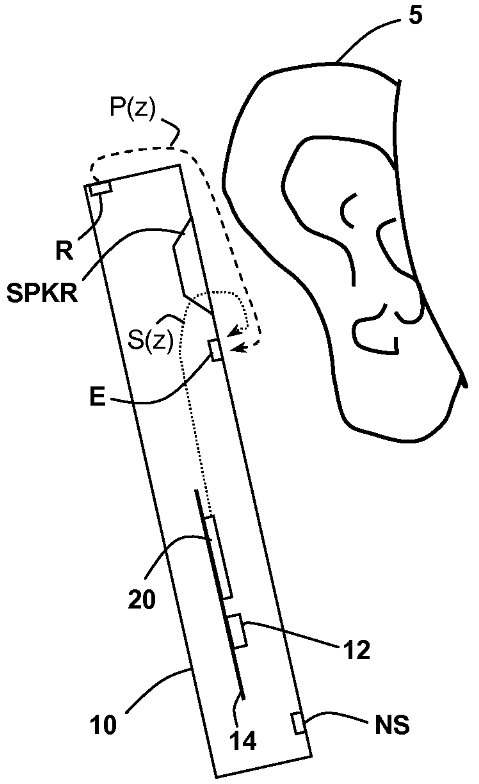
FIG. 1 is an illustration of a wireless telephone 10 in accordance with an embodiment of the present invention.

Referring now to FIG. 1, a wireless telephone 10 is illustrated in accordance with an embodiment of the present invention is shown in proximity to a human ear 5. Illustrated wireless telephone 10 is an example of a device in which techniques in accordance with embodiments of the invention may be employed, but it is understood that not all of the elements or configurations embodied in illustrated wireless telephone 10, or in the circuits depicted in subsequent illustrations, are required in order to practice the invention recited in the Claims. Wireless telephone 10 includes a transducer such as speaker SPKR that reproduces distant speech received by wireless telephone 10, along with other local audio event such as ringtones, stored audio program material, injection of near-end speech (i.e., the speech of the user of wireless telephone 10) to provide a balanced conversational perception, and other audio that requires reproduction by wireless telephone 10, such as sources from web-pages or other network communications received by wireless telephone 10 and audio indications such as battery low and other system event notifications. A near-speech microphone NS is provided to capture near-end speech, which is transmitted from wireless telephone 10 to the other conversation participant(s).

Wireless telephone 10 includes adaptive noise canceling (ANC) circuits and features that inject an anti-noise signal into speaker SPKR to improve intelligibility of the distant speech and other audio reproduced by speaker SPKR. A reference microphone R is provided for measuring the ambient acoustic environment, and is positioned away from the typical position of a user's mouth, so that the near-end speech is minimized in the signal produced by reference microphone R. A third microphone, error microphone E is provided in order to further improve the ANC operation by providing a measure of the ambient audio combined with the audio reproduced by speaker SPKR close to ear 5, when wireless telephone 10 is in close proximity to ear 5. Exemplary circuit 14 within wireless telephone 10 includes an audio CODEC integrated circuit 20 that receives the signals from reference microphone R, near speech microphone NS and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit.

In general, the ANC techniques of the present invention measure ambient acoustic events (as opposed to the output of speaker SPKR and/or the near-end speech) impinging on reference microphone R, and by also measuring the same ambient acoustic events impinging on error microphone E, the ANC processing circuits of illustrated wireless telephone 10 adapt an anti-noise signal generated from the output of reference microphone R to have a characteristic that minimizes the amplitude of the ambient acoustic events at error microphone E. Since acoustic path P(z) extends from reference microphone R to error microphone E, the ANC circuits are essentially estimating acoustic path P(z) combined with removing effects of an electro-acoustic path S(z) that represents the response of the audio output circuits of CODEC IC 20 and the acoustic/electric transfer function of speaker SPKR including the coupling between speaker SPKR and error microphone E in the particular acoustic environment, which is affected by the proximity and structure of ear 5 and other physical objects and human head structures that may be in proximity to wireless telephone 10, when wireless telephone 10 is not firmly pressed to ear 5. While the illustrated wireless telephone 10 includes a two microphone ANC system with a third near speech microphone NS, some aspects of the present invention may be practiced in a system that does not include separate error and reference microphones, or a wireless telephone that uses near speech microphone NS to perform the function of the reference microphone R. Also, in personal audio devices designed only for audio playback, near speech microphone NS will generally not be included, and the near-speech signal paths in the circuits described in further detail below can be omitted, without changing the scope of the invention, other than to limit the options provided for input to the microphone covering detection schemes.

Figure 2:
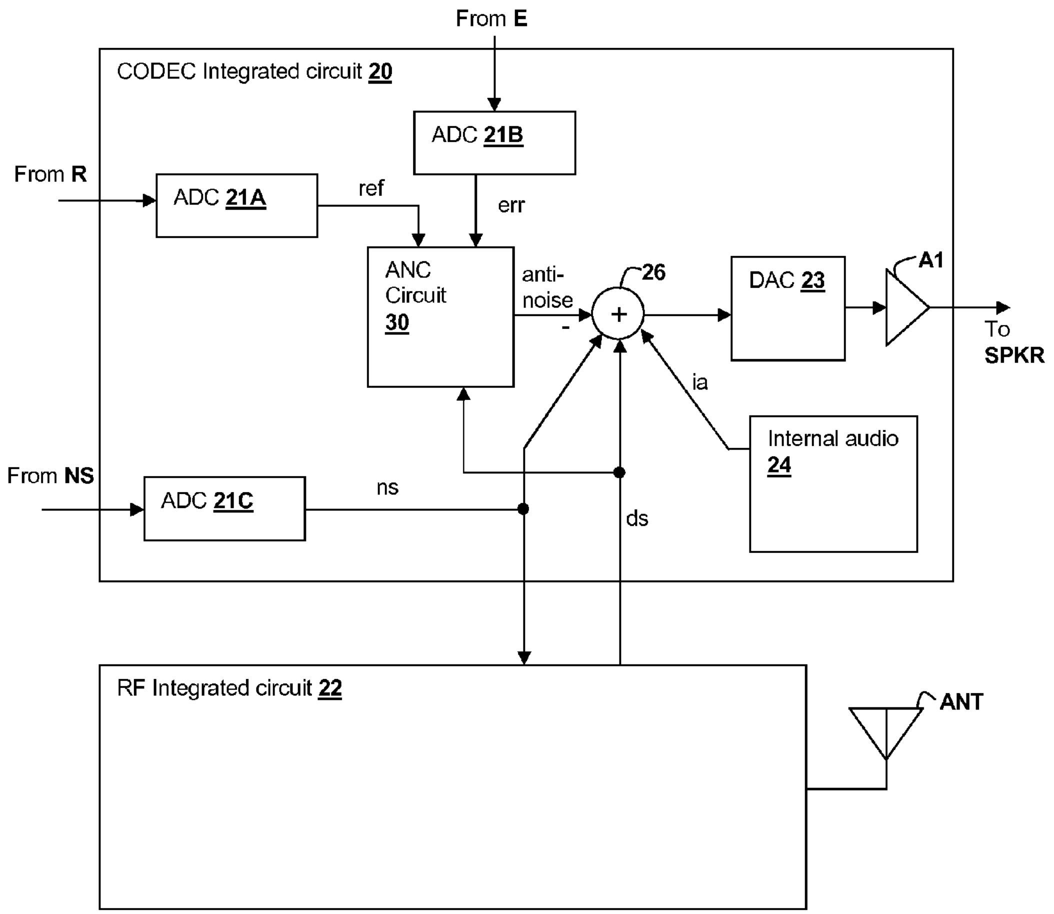
FIG. 2 is a block diagram of circuits within wireless telephone 10 in accordance with an embodiment of the present invention.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the error microphone signal. CODEC IC 20 generates an output for driving speaker SPKR from an amplifier A1, which amplifies the output of a digital-to-analog converter (DAC) 23 that receives the output of a combiner 26. Combiner 26 combines audio signals from internal audio sources 24, the anti-noise signal generated by ANC circuit 30, which by convention has the same polarity as the noise in reference microphone signal ref and is therefore subtracted by combiner 26, a portion of near speech signal ns so that the user of wireless telephone 10 hears their own voice in proper relation to downlink speech ds, which is received from radio frequency (RF) integrated circuit 22 and is also combined by combiner 26. Near speech signal ns is also provided to RF integrated circuit 22 and is transmitted as uplink speech to the service provider via antenna ANT.

Figure 3:
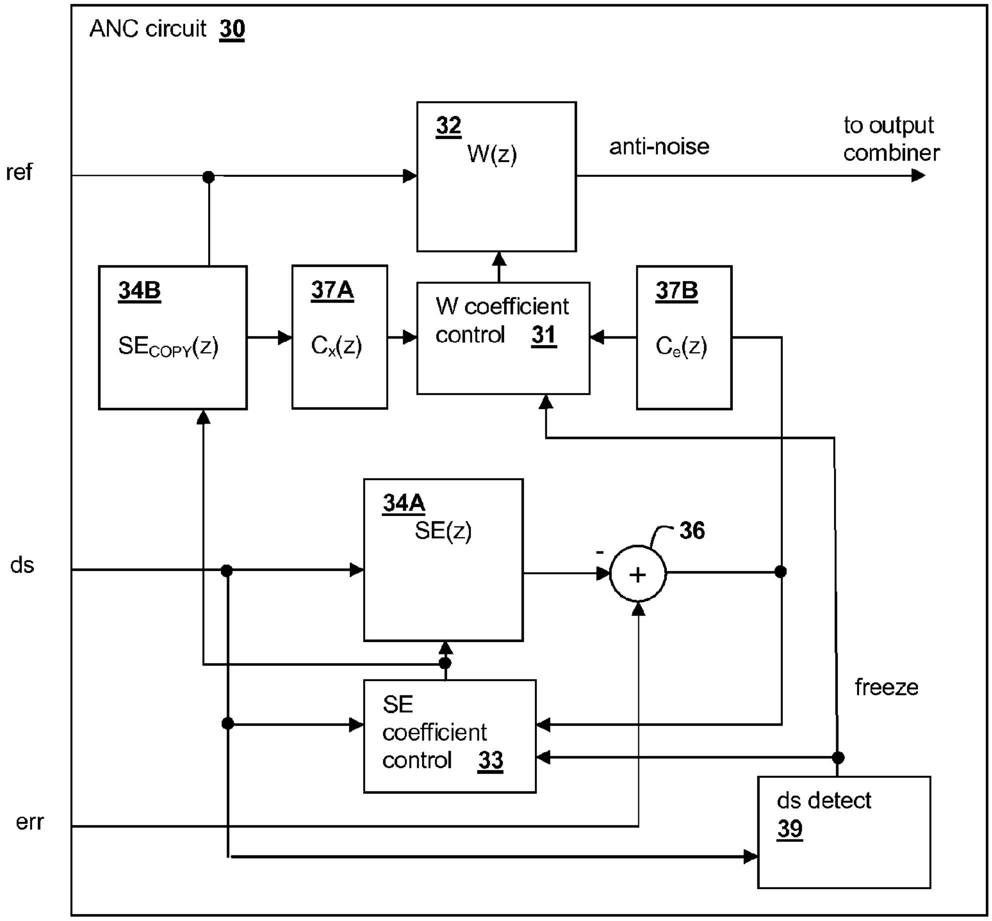
FIG. 3 is a block diagram depicting signal processing circuits and functional blocks within ANC circuit 30 of CODEC integrated circuit 20 of FIG. 2 in accordance with an embodiment of the present invention.

Referring now to FIG. 3, details of ANC circuit 30 are shown in accordance with an embodiment of the present invention. Adaptive filter 32 receives reference microphone signal ref and under ideal circumstances, adapts its transfer function W(z) to be P(z)/S(z) to generate the anti-noise signal, which is provided to an output combiner that combines the anti-noise signal with the audio to be reproduced by the transducer, as exemplified by combiner 26 of FIG. 2. The coefficients of adaptive filter 32 are controlled by a W coefficient control block 31 that uses a correlation of two signals to determine the response of adaptive filter 32, which generally minimizes the error, in a least-mean squares sense, between those components of reference microphone signal ref present in error microphone signal err. The signals compared by W coefficient control block 31 are the reference microphone signal ref as shaped by a copy of an estimate of the response of path S(z) provided by filter 34B and another signal that includes error microphone signal err. By transforming reference microphone signal ref with a copy of the estimate of the response of path S(z), response $SE_{COPY}(z)$, and minimizing the difference between the resultant signal and error microphone signal err, adaptive filter 32 adapts to the desired response of P(z)/S(z). A filter 37A that has a response $C_x(z)$ as explained in further detail below, processes the output of filter 34B and provides the first input to W coefficient control block 31. The second input to W coefficient control block 31 is processed by another filter 37B having a response of $C_e(z)$. Response $C_e(z)$ has a phase response matched to response $C_x(z)$ of filter 37A. Both filters 37A and 37B include a highpass response, so that DC offset and very low frequency variation are prevented from affecting the coefficients of W(z). In addition to error microphone signal err, the signal compared to the output of filter 34B by W coefficient control block 31 includes an inverted amount of downlink audio signal ds that has been processed by filter response SE(z), of which response $SE_{COPY}(z)$ is a copy. By injecting an inverted amount of downlink audio signal ds, adaptive filter 32 is prevented from adapting to the relatively large amount of downlink audio present in error microphone signal err and by transforming that inverted copy of downlink audio signal ds with the estimate of the response of path S(z), the downlink audio that is removed from error microphone signal err before comparison should match the expected version of downlink audio signal ds reproduced at error microphone signal err, since the electrical and acoustical path of S(z) is the path taken by downlink audio signal ds to arrive at error microphone E. Filter 34B is not an adaptive filter, per se, but has an adjustable response that is tuned to match the response of adaptive filter 34A, so that the response of filter 34B tracks the adapting of adaptive filter 34A.

To implement the above, adaptive filter 34A has coefficients controlled by SE coefficient control block 33, which compares downlink audio signal ds and error microphone signal err after removal of the above-described filtered downlink audio signal ds, that has been filtered by adaptive filter 34A to represent the expected downlink audio delivered to error microphone E, and which is removed from the output of adaptive filter 34A by a combiner 36. SE coefficient control block 33 correlates the actual downlink speech signal ds with the components of downlink audio signal ds that are present in error microphone signal err. Adaptive filter 34A is thereby adapted to generate a signal from downlink audio signal ds, that when subtracted from error microphone signal err, contains the content of error microphone signal err that is not due to downlink audio signal ds. A downlink audio detection block 39 determines when downlink audio signal ds contains information, e.g., the level of downlink audio signal ds is greater than a threshold amplitude. If no downlink audio signal ds is present, downlink audio detection block 39 asserts a control signal freeze that causes SE coefficient control block 33 and W coefficient control block 31 to halt adapting.

Figure 4:
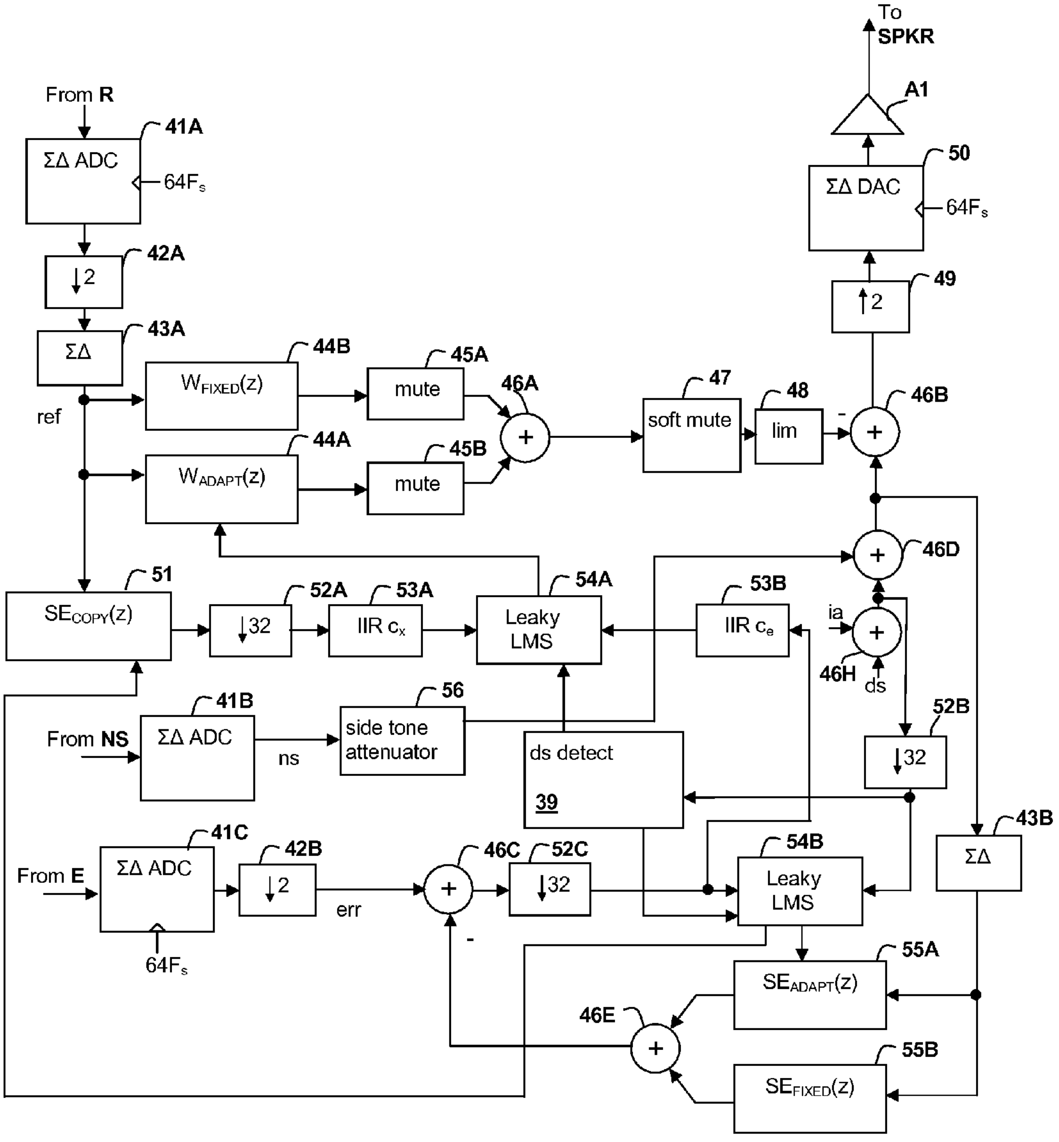
FIG. 4 is a block diagram depicting signal processing circuits and functional blocks within an integrated circuit in accordance with an embodiment of the present invention.

Referring now to FIG. 4, a block diagram of an ANC system is shown for illustrating ANC techniques in accordance with an embodiment of the invention as may be included in the embodiment of the invention depicted in FIG. 3, and as may be implemented within CODEC integrated circuit 20 of FIG. 2. Reference microphone signal ref is generated by a delta-sigma ADC 41A that operates at 64 times oversampling and the output of which is decimated by a factor of two by a decimator 42A to yield a 32 times oversampled signal. A sigma-delta shaper 43A is used to quantize reference microphone signal ref, which reduces the width of subsequent processing stages, e.g., filter stages 44A and 44B. Since filter stages 44A and 44B are operating at an oversampled rate, sigma-delta shaper 43A can shape the resulting quantization noise into frequency bands where the quantization noise will yield no disruption, e.g., outside of the frequency response range of speaker SPKR, or in which other portions of the circuitry will not pass the quantization noise. Filter stage 44B has a fixed response $W_{FIXED}$(z) that is generally predetermined to provide a starting point at the estimate of P(z)/S(z) for the particular design of wireless telephone 10 for a typical user. An adaptive portion $W_{ADAPT}$(z) of the response of the estimate of P(z)/S(z) is provided by adaptive filter stage 44A, which is controlled by a leaky least-means-squared (LMS) coefficient controller 54A. Leaky LMS coefficient controller MA is leaky in that the response normalizes to flat or otherwise predetermined response over time when no error input is provided to cause leaky LMS coefficient controller 54A to adapt. Providing a leaky controller prevents long-term instabilities that might arise under certain environmental conditions, and in general makes the system more robust against particular sensitivities of the ANC response.

In the system depicted in FIG. 4, reference microphone signal ref is filtered, by a filter 51 that has a response $SE_{COPY}$(z) that is an estimate of the response of path S(z), the output of which is decimated by a factor of 32 by a decimator 52A to yield a baseband audio signal that is provided, through an infinite impulse response (IIR) filter 53A to leaky LMS 54A. Filter 51 is not an adaptive filter, per se, but has an adjustable response that is tuned to match the combined response of adaptive filters 55A and 55B, so that the response of filter 51 tracks the adapting of response SE(z). The error microphone signal err is generated by a delta-sigma ADC 41C that operates at 64 times oversampling and the output of which is decimated by a factor of two by a decimator 42B to yield a 32 times oversampled signal. As in the system of FIG. 3, an amount of downlink audio ds that has been filtered by an adaptive filter to apply response SE(z) is removed from error microphone signal err by a combiner 46C, the output of which is decimated by a factor of 32 by a decimator 52C to yield a baseband audio signal that is provided, through an infinite impulse response (IIR) filter 53B to leaky LMS 54A. IIR filters 53A and 53B each include a high-pass response that prevents DC offset and very low frequency variations from affecting the adaptation of the coefficients of adaptive filter 44A.

Response SE(z) is produced by another parallel set of adaptive filter stages 55A and 55B, one of which, filter stage 55B has fixed response $SE_{FIXED}$(z), and the other of which, filter stage 55A has an adaptive response $SE_{ADAPT}$(z) controlled by leaky LMS coefficient controller MB. The outputs of adaptive filter stages 55A and 55B are combined by a combiner 46E. Similar to the implementation of filter response W(z) described above, response $SE_{FIXED}$(z) is generally a predetermined response known to provide a suitable starting point under various operating conditions for electrical/acoustical path S(z). Filter 51 is a copy of adaptive filter 55A/55B, but is not itself an adaptive filter, i.e., filter 51 does not separately adapt in response to its own output, and filter 51 can be implemented using a single stage or a dual stage. A separate control value is provided in the system of FIG. 4 to control the response of filter 51, which is shown as a single adaptive filter stage. However, filter 51 could alternatively be implemented using two parallel stages and the same control value used to control adaptive filter stage 55A could then be used to control the adjustable filter portion in the implementation of filter 51. The inputs to leaky LMS control block 54B are also at baseband, provided by decimating a combination of downlink audio signal ds and internal audio ia, generated by a combiner 46H, by a decimator 52B that decimates by a factor of 32, and another input is provided by decimating the output of a combiner 46C that has removed the signal generated from the combined outputs of adaptive filter stage 55A and filter stage 55B that are combined by another combiner 46E. The output of combiner 46C represents error microphone signal err with the components due to downlink audio signal ds removed, which is provided to LMS control block 54B after decimation by decimator 52C. The other input to LMS control block 54B is the baseband signal produced by decimator 52B. The level of downlink audio signal ds (and internal audio signal ia) at the output of decimator 52B is detected by downlink audio detection block 39, which freezes adaptation of LMS control blocks 54A, 54B when downlink audio signal ds and internal audio signal ia are absent.

The above arrangement of baseband and oversampled signaling provides for simplified control and reduced power consumed in the adaptive control blocks, such as leaky LMS controllers 54A and 54B, while providing the tap flexibility afforded by implementing adaptive filter stages 44A-44B, 55A-55B and filter 51 at the oversampled rates. The remainder of the system of FIG. 4 includes combiner 46H that combines downlink audio ds with internal audio ia, the output of which is provided to the input of a combiner 46D that adds a portion of near-end microphone signal ns that has been generated by sigma-delta ADC 41B and filtered by a sidetone attenuator 56 to provide balanced conversation perception. The output of combiner 46D is shaped by a sigma-delta shaper 43B that provides inputs to filter stages 55A and 55B that, in a manner similar to sigma-delta shaper 43A as described above, permits the width of filter stages 55A and 55B to be reduced by quantizing the output of combiner 46D. The quantization noise of sigma-delta shaper 43B is removed by the inherent low-pass response of decimator 52C.

In accordance with an embodiment of the invention, the output of combiner 46D is also combined with the output of adaptive filter stages 44A-44B that have been processed by a control chain that includes a corresponding hard mute block 45A, 45B for each of the filter stages, a combiner 46A that combines the outputs of hard mute blocks 45A, 45B, a soft mute 47 and then a soft limiter 48 to produce the anti-noise signal that is subtracted by a combiner 46B with the source audio output of combiner 46D. The output of combiner 46B is interpolated up by a factor of two by an interpolator 49 and then reproduced by a sigma-delta DAC 50 operated at the 64× oversampling rate. The output of DAC 50 is provided to amplifier A1, which generates the signal delivered to speaker SPKR.

Figure 5:
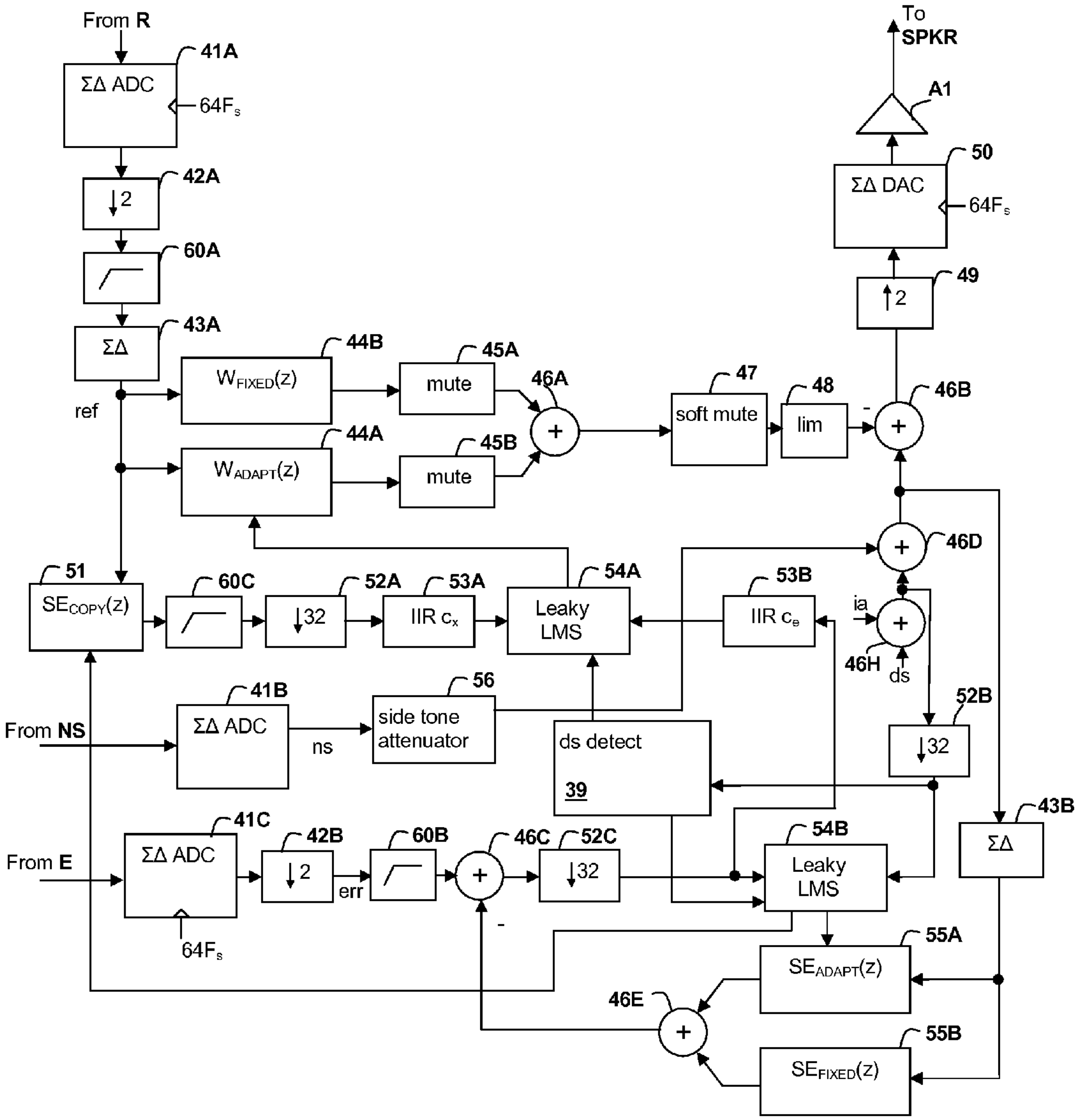
FIG. 5 is a block diagram depicting signal processing circuits and functional blocks within an integrated circuit in accordance with another embodiment of the present invention.

Referring now to FIG. 5, a block diagram of an ANC system is shown for illustrating ANC techniques in accordance with another embodiment of the invention that may be included in the embodiment of the invention depicted in FIG. 3, and as may be implemented within CODEC integrated circuit 20 of FIG. 2. The ANC system of FIG. 5 is similar to that of FIG. 4, so only differences between them will be described in detail below. Rather than providing a high-pass response at the inputs to leaky LMS 54A, DC components are removed directly from reference microphone signal ref and error microphone signal err by providing respective high-pass filters 60A and 60B in the reference and error microphone signal paths. An additional high-pass filter 60C is then included in the SE copy signal path after filter 51. The architecture illustrated in FIG. 5 is advantageous in that high-pass filter 60A removes DC and low frequency components from the anti-noise signal path and that otherwise would be passed by filter stages 44A, 44B in the anti-noise signal provided to speaker SPKR, wasting energy, generating heat and consuming dynamic range. However, since reference microphone signal ref needs to contain some low-frequency information in frequency bands that can be canceled by the ANC system, i.e., in frequency ranges for which speaker SPKR has significant response, filter 60A is designed to pass such frequencies, while for optimum adaptation of leaky LMS MA, a higher high-pass cut-in frequency, e.g., 200 Hz is employed. The phase response of filters 60B and 60C is matched to maintain a stable operating condition for leaky LMS 54A.

Each or some of the elements in the systems of FIG. 4 and FIG. 5, as well in as the exemplary circuits of FIG. 2 and FIG. 3, can be implemented directly in logic, or by a processor such as a digital signal processing (DSP) core executing program instructions that perform operations such as the adaptive filtering and LMS coefficient computations. While the DAC and ADC stages are generally implemented with dedicated mixed-signal circuits, the architecture of the ANC system of the present invention will generally lend itself to a hybrid approach in which logic may be, for example, used in the highly oversampled sections of the design, while program code or microcode-driven processing elements are chosen for the more complex, but lower rate operations such as computing the taps for the adaptive filters and/or responding to detected events such as those described herein.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

a reference microphone mounted on the housing for providing a reference microphone signal indicative of the ambient audio sounds;

an error microphone mounted on the housing in proximity to the transducer for providing an error microphone signal indicative of the acoustic output of the transducer and the ambient audio sounds at the transducer;

a processing circuit that implements an adaptive filter having a response that generates the anti-noise signal from the reference microphone signal to reduce the presence of the ambient audio sounds heard by the listener, wherein the processing circuit implements a coefficient control block that shapes the response of the adaptive filter in conformity with the error microphone signal and the reference microphone signal by adapting the response of the adaptive filter to minimize the ambient audio sounds at the error microphone, wherein a first sample rate of the adaptive filter is substantially higher than a second sample rate at which the coefficient control block operates, wherein the source audio has a sample rate equal to or less than the second sample rate;

an interpolator included in the processing circuit that converts the source audio to the first sample rate; and a combiner included in the processing circuit that combines the anti-noise signal and an output of the interpolator to generate the audio signal at the first sample rate.

2. The personal audio device of claim 1, wherein the processing circuit implements a secondary path adaptive filter having a secondary path response that shapes the source audio and another combiner that removes the source audio from the error microphone signal to provide an error signal indicative of the combined anti-noise and ambient audio sounds delivered to the listener, wherein the secondary path adaptive filter is also operated at the first sample rate, and wherein updates of coefficients of the secondary path adaptive filter are performed at a rate equal to or lower than the second sample rate.

3. A method of canceling ambient audio sounds in the proximity of a transducer of a personal audio device, the method comprising:

first measuring ambient audio sounds with a reference microphone to produce a reference microphone signal;

second measuring an output of the transducer and the ambient audio sounds at the transducer with an error microphone;

adaptively generating an anti-noise signal from a result of the first measuring and a result of the second measuring for countering the effects of the ambient audio sounds at an acoustic output of the transducer by adapting a response of an adaptive filter that filters an output of the reference microphone;

combining the anti-noise signal with a source audio signal to generate an audio signal provided to the transducer, wherein the anti-noise signal is generated at a first sample rate that is substantially higher than a second sample rate of a coefficient control of the adaptive filter, wherein the source audio has a sample rate equal to or less than the second sample rate;

converting the source audio to the first sample rate by interpolation; and combining the anti-noise signal and a result of the converting to generate the audio signal at the first sample rate.

4. The method of claim 3, further comprising:

shaping a copy of the source audio with a secondary path response with a secondary path adaptive filter operating at the first sample rate;

removing the result of the shaping the copy of the source audio from the error microphone signal to produce an error signal indicative of the combined anti-noise and ambient audio sounds; and updating coefficients of the secondary path adaptive filter at a rate equal to or lower than the second sample rate.

5. An integrated circuit for implementing at least a portion of a personal audio device, comprising:

an output for providing a signal to a transducer including both source audio for playback to a listener and an anti-noise signal for countering the effects of ambient audio sounds in an acoustic output of the transducer;

a reference microphone input for receiving a reference microphone signal indicative of the ambient audio sounds;

an error microphone input for receiving an error microphone signal indicative of the acoustic output of the transducer and the ambient audio sounds at the transducer;

a processing circuit that implements an adaptive filter having a response that generates the anti-noise signal from the reference microphone signal to reduce the presence of the ambient audio sounds heard by the listener, wherein the processing circuit implements a coefficient control block that shapes the response of the adaptive filter in conformity with the error microphone signal and the reference microphone signal by adapting the response of the adaptive filter to minimize the ambient audio sounds at the error microphone, wherein a first sample rate of the adaptive filter is substantially higher than a second sample rate at which the coefficient control block operates, wherein the source audio has a sample rate equal to or less than the second sample rate;

an interpolator included in the processing circuit that converts the source audio to the first sample rate; and a combiner included in the processing circuit that combines the anti-noise signal and an output of the interpolator to generate the audio signal at the first sample rate.

6. The integrated circuit of claim 5, wherein the processing circuit implements a secondary path adaptive filter having a secondary path response that shapes the source audio and another combiner that removes the source audio from the error microphone signal to provide an error signal indicative of the combined anti-noise and ambient audio sounds delivered to the listener, wherein the secondary path adaptive filter is also operated at the first sample rate, and wherein updates of coefficients of the secondary path adaptive filter are performed at a rate equal to or lower than the second sample rate.

7. A personal audio device, comprising:

a personal audio device housing;

an audio source having an output providing source audio for playback to a listener;

a transducer mounted on the housing for reproducing an audio signal;

a combiner for combining the source audio and an anti-noise signal for countering the effects of ambient audio sounds in an acoustic output of the transducer, to generate the audio signal;

a reference microphone mounted on the housing for providing a reference microphone signal indicative of the ambient audio sounds;

an error microphone mounted on the housing in proximity to the transducer for providing an error microphone signal indicative of the acoustic output of the transducer and the ambient audio sounds at the transducer; and a processing circuit that implements an adaptive filter having a response that generates the anti-noise signal from the reference microphone signal to reduce the presence of the ambient audio sounds heard by the listener, wherein the processing circuit implements a coefficient control block that shapes the response of the adaptive filter by adjusting coefficients that determine the response of the adaptive filter in conformity with the error microphone signal and the reference microphone signal to minimize the ambient audio sounds at the error microphone, wherein the processing circuit detects whether or not the source audio is present at the output of the audio source, and in response to detecting that the source audio is not present, halts adjustment of the coefficients while continuing to generate the anti-noise signal.

8. The personal audio device of claim 7, wherein adjustment of the coefficients is re-commenced upon detection of the source audio subsequent to the halting of the adjustment of the coefficients.

9. A method of canceling ambient audio sounds in the proximity of a transducer of a personal audio device, the method comprising:

first measuring ambient audio sounds with a reference microphone;

providing source audio from an audio source;

second measuring an output of the transducer and the ambient audio sounds at the transducer with an error microphone;

adaptively generating an anti-noise signal from a result of the first measuring and a result of the second measuring for countering the effects of ambient audio sounds at an acoustic output of the transducer by adjusting coefficients that determine the response of an adaptive filter that filters an output of the reference microphone;

combining the source audio with the anti-noise signal;

reproducing the combined source audio and anti-noise signal by the transducer;

detecting whether or not the source audio is present at an output of the audio source;

responsive to detecting that the source audio is not present, halting adjustment of the coefficients while continuing to generate the anti-noise signal.

10. The method of claim 9, wherein the adjusting coefficients comprises re-commencing adaptation of the adaptive filter upon detection of the source audio subsequent to the halting of the adjustment of the coefficients.

11. An integrated circuit for implementing at least a portion of a personal audio device, comprising:

an audio source having an output providing source audio for playback to a listener;

a combiner for combining the source audio and an anti-noise signal for countering the effects of ambient audio sounds in an acoustic output of a transducer, to generate an audio signal;

an output for providing the audio signal to the transducer;

a reference microphone input for receiving a reference microphone signal indicative of the ambient audio sounds;

an error microphone input for receiving an error microphone signal indicative of the acoustic output of the transducer and the ambient audio sounds at the transducer; and a processing circuit that implements an adaptive filter having a response that generates the anti-noise signal from the reference microphone signal to reduce the presence of the ambient audio sounds heard by the listener, wherein the processing circuit implements a coefficient control block that shapes the response of the adaptive filter by adjusting coefficients that determine the response of the adaptive filter in conformity with the error microphone signal and the reference microphone signal to minimize the ambient audio sounds at the error microphone, wherein the processing circuit detects whether or not the source audio is present at the output of the audio source, and in response to detecting that the source audio is not present, halts adjustment of the coefficients while continuing to generate the anti-noise signal.

12. The integrated circuit of claim 11, wherein adjustment of the coefficients is re-commenced upon detection of the source audio subsequent to the halting of the adjustment of the coefficients.

13. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

a reference microphone mounted on the housing for providing a reference microphone signal indicative of the ambient audio sounds;

a first analog-to-digital converter for converting the reference microphone signal to a reference microphone digital representation;

an error microphone mounted on the housing in proximity to the transducer for providing an error microphone signal indicative of the acoustic output of the transducer and the ambient audio sounds at the transducer;

a second analog-to-digital converter for converting the error microphone signal to an error microphone digital representation; and a processing circuit that implements an adaptive filter having a response that generates the anti-noise signal from the reference microphone digital representation to reduce the presence of the ambient audio sounds heard by the listener, wherein the processing circuit implements a coefficient control block that shapes the response of the adaptive filter in conformity with the error microphone digital representation and the reference microphone digital representation by adapting the response of the adaptive filter to minimize the ambient audio sounds at the error microphone, wherein the processing circuit further implements a first digital filter having a first high-pass characteristic coupled between the first analog-to-digital converter and an input to the adaptive filter from which the anti-noise signal is generated for removing first DC components from the input to the adaptive filter, and wherein the processing circuit further implements a second digital filter having a second high-pass characteristic that differs from the first high-pass characteristic coupled between the first analog-to-digital converter and the coefficient control block for removing second DC components from a first input to the coefficient control block.

14. The personal audio device of claim 13, wherein the processing circuit further implements a third digital filter having a third high-pass characteristic coupled between second analog-to-digital converter and the coefficient control block for removing third DC components from a third input to the coefficient control block.

15. The personal audio device of claim 14, wherein the first digital filter has a cut-in frequency of approximately 200 Hz and wherein the second digital filter has a cut-in frequency substantially below 200 Hz in frequency bands in which the transducer has significant response.

16. A method of canceling ambient audio sounds in the proximity of a transducer of a personal audio device, the method comprising:

first measuring ambient audio sounds with a reference microphone;

first converting a result of the first measuring to a first digital representation;

second measuring an output of the transducer and the ambient audio sounds at the transducer with an error microphone;

second converting a result of the second measuring to a second digital representation;

first filtering the first digital representation with a first digital high-pass filter;

second filtering the first digital representation with a second digital high-pass filter having a response that differs from a response of the first digital high-pass filter; and adaptively generating an anti-noise signal from a result of the first filtering for countering the effects of ambient audio sounds at an acoustic output of the transducer by adapting a response of an adaptive filter that filters the result of the first filtering, wherein the first filtering acts to remove first DC components from an input to the adaptive filter, and wherein a response of the adaptive filter is adjusted according to a coefficient control block that receives a result of the second filtering and the second digital representation, and wherein the second filtering acts to remove first DC components from a first input to a coefficient control block that controls the adaptive filter.

17. The method of claim 16, further comprising third filtering the second digital representation with a third digital high-pass filter to remove the second DC components from a second input to the coefficient control block.

18. The method of claim 16, wherein the first digital filter has a cut-in frequency of approximately 200 Hz and the second digital filter has a cut-in frequency substantially below 200 Hz in bands in which the transducer has significant response.

19. An integrated circuit for implementing at least a portion of a personal audio device, comprising:

an output for providing a signal to a transducer including both source audio for playback to a listener and an anti-noise signal for countering the effects of ambient audio sounds in an acoustic output of the transducer;

a reference microphone input for receiving a reference microphone signal indicative of the ambient audio sounds;

a first analog-to-digital converter for converting the reference microphone signal to a reference microphone digital representation;

an error microphone input for receiving an error microphone signal indicative of the acoustic output of the transducer and the ambient audio sounds at the transducer; and a second analog-to-digital converter for converting the error microphone signal to an error microphone digital representation; and a processing circuit that implements an adaptive filter having a response that generates the anti-noise signal from the reference microphone digital representation to reduce the presence of the ambient audio sounds heard by the listener, wherein the processing circuit implements a coefficient control block that shapes the response of the adaptive filter in conformity with the error microphone digital representation and the reference microphone digital representation by adapting the response of the adaptive filter to minimize the ambient audio sounds at the error microphone, wherein the processing circuit further implements a first digital filter having a first high-pass characteristic coupled between the first analog-to-digital converter and an input to the adaptive filter from which the anti-noise signal is generated for removing first DC components from the input to the adaptive filter, and wherein the processing circuit further implements a second digital filter having a second high-pass characteristic that differs from the first high-pass characteristic coupled between the first analog-to-digital converter and the coefficient control block for removing second DC components from a first input to the coefficient control block.

20. The integrated circuit of claim 19, wherein the processing circuit further implements a third digital filter having a third high-pass characteristic coupled between the second analog-to-digital converter and the coefficient control block for removing the third DC components from a third input to the coefficient control block.

21. The integrated circuit of claim 20, wherein the first digital filter has a cut-in frequency of approximately 200 Hz and wherein the second digital filter has a cut-in frequency substantially below 200 Hz in frequency bands in which the transducer has significant response.

22. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

a reference microphone mounted on the housing for providing a reference microphone signal indicative of the ambient audio sounds;

a first analog-to-digital converter for converting the reference microphone signal to a first reference microphone signal digital representation at a first sample rate;

a first sigma-delta quantizer that quantizes the first digital representation at the first sample rate to generate a lowered resolution second reference microphone signal digital representation at the first sample rate; and a processing circuit that implements an adaptive filter having a response that generates the anti-noise signal from the lowered resolution second reference microphone signal digital representation to reduce the presence of the ambient audio sounds heard by the listener, wherein the processing circuit implements a coefficient control block that shapes the response of the adaptive filter in conformity with the reference microphone signal by adapting the response of the adaptive filter.

23. The personal audio device of claim 22, wherein the source audio is a digital source audio representation, and wherein the personal audio device further comprises:

a second delta-sigma quantizer that quantizes the digital source audio representation to generate a lowered resolution digital source audio representation; and an error microphone mounted on the housing in proximity to the transducer for providing an error microphone signal indicative of the acoustic output of the transducer and the ambient audio sounds at the transducer, wherein the processing circuit implements a secondary path adaptive filter having a secondary path response that filters the lowered resolution digital source audio representation to produce a filtered source audio representation and a combiner that removes the filtered source audio representation from the error microphone signal to provide an error signal to the coefficient control block that is indicative of the combined anti-noise and ambient audio sounds delivered to the listener.

24. A method of canceling ambient audio sounds in the proximity of a transducer of a personal audio device, the method comprising:

first measuring ambient audio sounds with a reference microphone;

converting the reference microphone signal to generate a first reference microphone digital representation at a firsst sample rate using an analog-to-digital converter;

quantizing the first reference microphone signal digital representation at the first sample rate to generate a lowered resolution second reference microphone signal digital representation at the first sample rate using a sigma-delta shaper; and adaptively generating an anti-noise signal from the lowered resolution second reference microphone signal digital representation for countering the effects of ambient audio sounds at an acoustic output of the transducer by adapting a response of an adaptive filter that filters the lowered resolution second reference microphone signal digital representation.

25. The method of claim 24, further comprising:

quantizing a digital source audio representation to generate a lowered resolution digital source audio representation; and second measuring an output of the transducer and the ambient audio sounds at the transducer with an error microphone, wherein the adaptively generating includes filtering the lowered resolution digital source audio representation with a secondary path adaptive filter having a secondary path response that shapes the lowered resolution digital source audio representation, and removing a resulting output of the secondary path adaptive filter from the error microphone signal to provide an error signal indicative of the combined anti-noise and ambient audio sounds delivered to the listener.

26. An integrated circuit for implementing at least a portion of a personal audio device, comprising:

an output for providing a signal to a transducer including both source audio for playback to a listener and an anti-noise signal for countering the effects of ambient audio sounds in an acoustic output of the transducer;

a reference microphone input for receiving a reference microphone signal indicative of the ambient audio sounds;

a first analog-to-digital converter for converting the reference microphone signal to a first reference microphone signal digital representation at a first sample rate;

a first sigma-delta quantizer that quantizes the first digital representation at the first sample rate to generate a lowered resolution second reference microphone signal digital representation at the first sample rate; and a processing circuit that implements an adaptive filter having a response that generates the anti-noise signal from the lowered resolution second reference microphone signal digital representation to reduce the presence of the ambient audio sounds heard by the listener, wherein the processing circuit implements a coefficient control block that shapes the response of the adaptive filter in conformity with the reference microphone signal by adapting the response of the adaptive filter.

27. The integrated circuit of claim 26, wherein the source audio is a digital source audio representation, and wherein the integrated circuit further comprises:

a second delta-sigma quantizer that quantizes the digital source audio representation to generate a lowered resolution digital source audio representation; and an error microphone input for receiving an error microphone signal indicative of the acoustic output of the transducer and the ambient audio sounds at the transducer, wherein the processing circuit implements a secondary path adaptive filter having a secondary path response that filters the lowered resolution digital source audio representation to produce a filtered source audio representation and a combiner that removes the filtered source audio representation from the error microphone signal to provide an error signal to the coefficient control block that is indicative of the combined anti-noise and ambient audio sounds delivered to the listener.

* * * * *